United States Patent
Kurihara et al.

(10) Patent No.: US 11,389,494 B2
(45) Date of Patent: Jul. 19, 2022

(54) COMPOSITION FOR SUPPRESSING OR IMPROVING EYE FATIGUE

(71) Applicant: Kirin Holdings Kabushiki Kaisha, Tokyo (JP)

(72) Inventors: Toshihide Kurihara, Shinjuku-ku (JP); Yuji Morita, Nakano-ku (JP); Kenta Jonai, Nakano-ku (JP); Daisuke Fujiwara, Nakano-ku (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 372 days.

(21) Appl. No.: 16/331,849

(22) PCT Filed: Sep. 8, 2017

(86) PCT No.: PCT/JP2017/032398
§ 371 (c)(1),
(2) Date: Mar. 8, 2019

(87) PCT Pub. No.: WO2018/047930
PCT Pub. Date: Mar. 15, 2018

(65) Prior Publication Data
US 2019/0374587 A1 Dec. 12, 2019

(30) Foreign Application Priority Data

Sep. 9, 2016 (JP) .............................. JP2016-177039

(51) Int. Cl.
*A61K 35/747* (2015.01)
*A23L 33/135* (2016.01)
*A61P 27/02* (2006.01)

(52) U.S. Cl.
CPC .......... *A61K 35/747* (2013.01); *A23L 33/135* (2016.08); *A61P 27/02* (2018.01)

(58) Field of Classification Search
None
See application file for complete search history.

(56) References Cited

U.S. PATENT DOCUMENTS

| 2006/0088513 | A1 | 4/2006 | Inoue et al. |
| 2009/0312438 | A1 | 12/2009 | Bernstein et al. |
| 2013/0302380 | A1 | 11/2013 | Fujiwara et al. |
| 2018/0207187 | A1 | 7/2018 | Nakazawa et al. |

FOREIGN PATENT DOCUMENTS

| JP | 2005-137357 | | 6/2005 |
| JP | 2013-501706 | A | 1/2013 |
| JP | 2016-073314 | A | 5/2016 |
| WO | WO-2004/096246 | A1 | 11/2004 |
| WO | WO-2014/132982 | A1 | 9/2014 |
| WO | WO-2017/010520 | A1 | 1/2017 |

OTHER PUBLICATIONS

Rosenfield (Optometry in Practice vol. 17 Issue 1, pp. 1-10).*
Morita et al., "Effect of Heat-Killed *Lactobacillus paracasei* KW3110 Ingestion on Ocular Disorders Caused by Visual Display Terminal (VDT) Loads: A Randomized, Double-Blind, Placebo-Controlled Parallel-Group Study," Nutrients, Aug. 9, 2018, 10(8):1058, 17 pages.
Supplementary European Search Report dated Feb. 5, 2020, in EP 17848868.0.
"Uncured Eye Fatigue—What is "asthenopia"?", Healthcare University, dated Jul. 1, 2014, retrieved from: http://www.skincare-univ.com/article/004789/, 4 pages.
JP International Preliminary Report on Patentability for Appl. Ser. No. PCT/JP2017/032398, dated Sep. 8, 2017, 14 pages.
Suzuki, M., "Retinal Blue Light Toxicity", Ganka, vol. 55 No. 7, pp. 769-772, dated 2013, 10 pages.
Tsubota, K., Ganka, vol. 55 No. 7, pp. 761-762, dated 2013, 2 pages.
Tsubota, K., Ganka, vol. 55, pp. 763-767, dated 2013, 5 pages.
Tsushin, Suzuran-Shoku, "Eye fatigue—Are your eyes fatigued?" 2012, retrieved from: http://horon-suzuran.co.jp/wp-content/themes/horon-suzuran/old/docs/NO.189.pdf, 5 pages.
Yan, F. et al., "Probiotics and Immune Health", Current Opinion in Gastroenterology, 2011, vol. 27, pp. 496-501.

* cited by examiner

*Primary Examiner* — Robert A Zeman
(74) *Attorney, Agent, or Firm* — Foley & Lardner LLP

(57) ABSTRACT

An object of the present invention is to provide a composition for preventing visual dysfunction caused by exposure to light, such as so-called blue light. The present invention provides a composition comprising a lactic acid bacterium as an active ingredient for use in suppressing or improving conditions caused by retinal inflammation resulting from light damage. Eye discomfort is an exemplary condition caused by retinal inflammation resulting from light damage.

5 Claims, 4 Drawing Sheets

A

B

COMPOSITION FOR SUPPRESSING OR IMPROVING EYE FATIGUE

CROSS-REFERENCE TO RELATED APPLICATIONS

This application is a National Stage application of PCT/JP2017/032398, filed Sep. 8, 2017, which claims priority from Japanese Patent Application No. 2016-177039, filed on Sep. 9, 2016, the entire disclosures of which are incorporated herein by reference.

TECHNICAL FIELD

The present invention relates to a composition for suppressing or improving eye fatigue. The present invention also relates to a composition for suppressing retinal damages or disorders resulting from light damage.

BACKGROUND ART

Widespread use of LED lights, personal computers, and smartphones increasingly makes VDT (Visual Display Terminal) work indispensable in daily life, while the possible accompanying overuse of eyes during VDT work and the resulting eye damage by blue light are now pointed out (Non-Patent Documents 1 and 2). It means that maintenance and improvement of visual functions is required by people of all ages, from young to old.

Oxidative stress has been reported as one of the factors for retinal disorders resulting from light damage caused by, for example, blue light, and antioxidants as substances for maintenance of visual functions are researched and developed. For example, substances such as lutein are reported as effective antioxidants for improving contrast sensitivity function, which is one of the visual functions (Patent Document 1), but these substances have only limited applications to foods and drinks because of their problems such as solubility. Thus, there is a demand for such substances that can be easily ingested on a daily basis.

Retinal disorders resulting from light damage are widely being recognized as a kind of inflammation in a broad sense (Non-Patent Document 3). If such inflammation can be controlled, reduction of visual functions due to retinal disorders may be prevented. However, there have been a few studies reporting success in preventing the reduction of visual functions by such a mechanism.

Probiotics such as lactic acid bacteria are reported to have immunoregulatory effects such as, for example, anti-inflammatory effect, anti-allergy effect, anti-infection effect, and immunopotentiation effect (for example, Non-Patent Document 4). For example, *Lactobacillus paracasei* strain KW3110 has been reported as a lactic acid bacterium useful for, for example, treatment of allergies (Patent Document 2 and the like). However, there is no report on lactic acid bacteria that contribute to amelioration of emerging social problems in recent years, namely retinal disorders and reduced visual functions caused by blue light.

If any component useful for maintenance and improvement of visual functions can be identified in foods that can be consumed on a daily basis, such a component will be useful for people of all ages. If any bacterium useful for maintenance and improvement of visual functions can be identified, particularly among those lactic acid bacteria that are commonly consumed, such a lactic acid bacterium can be used for development of products available for people of all ages, from young to old, by using the bacterium as an ingredient for foods and drinks.

REFERENCE LIST

Patent Documents

Patent Document 1: JP 2013-501706 T
Patent Document 2: JP 2005-137357 A

Non-Patent Documents

Non-Patent Document 1: Kazuo Tsubota, (2013) Ophthalmology, 55(7), 761-762
Non-Patent Document 2: Kazuo Tsubota, (2013) Ophthalmology, 55(7), 763-767
Non-Patent Document 3: Mihoko Suzuki, (2013) Ophthalmology, 55(7), 769-772
Non-Patent Document 4: Yan, F., Curr. Opin. Gastroenterol, 27, 496-501, (2011)

SUMMARY OF THE INVENTION

An object of the present invention is to provide a composition for preventing visual dysfunction caused by exposure to light, such as so-called blue light.

The inventors studied the effects of lactic acid bacteria on visual functions. When human myeloid dendritic cells (mDCs) were cultured in the presence of a lactic acid bacterium, *Lactobacillus paracasei* strain KW3110, the inventors found that the supernatant from the mDC culture suppressed cell death of retinal pigment epithelial cells caused by exposure to blue light. Additionally, exposure of mice to blue light results in a light damage-induced decrease in retinal outer nuclear layer thickness. However, the inventors found that mice fed with a lactic acid bacterium, *Lactobacillus paracasei* strain KW3110, maintained the retinal outer nuclear layer thickness even under blue light exposure. Consequently, the inventors found that oral ingestion of a composition comprising a lactic acid bacterium can suppress reduction of visual functions, and thereby completed the present invention.

That is, the present invention is as follows.

[1] A composition and an agent for use in suppressing or improving eye fatigue, comprising a lactic acid bacterium as an active ingredient.

[2] The composition and the agent according to [1], wherein said eye fatigue is asthenopia.

[3] The composition and the agent according to [1] or [2], wherein said eye fatigue is induced by light stimulation.

[4] A composition and an agent for use in suppressing or improving conditions caused by retinal inflammation resulting from light damage, comprising a lactic acid bacterium as an active ingredient.

[5] The composition and the agent according to [4], wherein said condition caused by retinal inflammation resulting from light damage is decrease in retinal thickness.

[6] The composition and the agent according to [4], wherein said condition caused by retinal inflammation resulting from light damage is eye discomfort.

[7] The composition and the agent according to [6], wherein said eye discomfort is objectively or subjectively perceived eye fatigue, or dry eye.

[8] The composition and the agent according to [6], wherein said condition caused by retinal inflammation resulting from light damage is stiffness of the shoulder or lower back, or dull headache.

[9] A composition and an agent for use in suppressing cell death of retinal pigment epithelial cells or decrease in retinal thickness, or for use in protecting visual functions under visible light, comprising a lactic acid bacterium as an active ingredient.

[10] The composition and the agent according to [9], wherein said cell death of retinal pigment epithelial cells or said decrease in retinal thickness is induced by light stimulation.

[11] The composition and the agent according to any of [3] to [8] and [10], wherein the light causing said light stimulation and said light damage has a wavelength of 380 nm to 530 nm.

[12] The composition and the agent according to any of [1] to [11], wherein said lactic acid bacterium is a bacterium belonging to the genus *Lactobacillus*.

[13] The composition and the agent according to any of [1] to [12], wherein said lactic acid bacterium is *Lactobacillus paracasei*.

[14] The composition and the agent according to any of [1] to [13], wherein said lactic acid bacterium is *Lactobacillus paracasei* strain KW3110.

[15] The composition and the agent according to any of [1] to [14], which are in the form of a food.

[16] The composition and the agent according to any of [1] to [15], which are in the form of a supplement.

[17] A method for suppressing or improving eye fatigue, a method for suppressing or improving conditions caused by retinal inflammation resulting from light damage, a method for suppressing cell death of retinal pigment epithelial cells or decrease in retinal thickness, and a method for protecting visual functions under visible light, each comprising feeding or administering an effective amount of a lactic acid bacterium to a mammal, including a human.

[18] Use of a lactic acid bacterium for the manufacture of an agent for suppressing or improving eye fatigue, for the manufacture of an agent for suppressing or improving conditions caused by retinal inflammation resulting from light damage, or for the manufacture of an agent for suppressing cell death of retinal pigment epithelial cells or decrease in retinal thickness or an agent for protecting visual functions under visible light.

[19] Use of a lactic acid bacterium as an agent for suppressing or improving eye fatigue, as an agent for suppressing or improving conditions caused by retinal inflammation resulting from light damage, or as an agent for suppressing cell death of retinal pigment epithelial cells or decrease in retinal thickness or an agent for protecting visual functions under visible light.

[20] A lactic acid bacterium for use in suppressing or improving eye fatigue, for use in suppressing or improving conditions caused by retinal inflammation resulting from light damage, for use in suppressing cell death of retinal pigment epithelial cells or decrease in retinal thickness, or for use in protecting visual functions under visible light.

In this specification, the composition according to [1], [4], and [9] may referred to as "the compositions of the present invention." In this specification, the agents according to [1], [4], and [9] may also be referred to as "the agents of the present invention."

The composition and the agent of the present invention can prevent visual dysfunction caused by exposure to light, such as blue light, and can suppress or improve conditions caused by retinal inflammation resulting from light damage. Since lactic acid bacteria have long been safely consumed in the form of foods such as yogurt, the compositions and the agents of the present invention are safe and are unlikely harmful even if they are consumed for a long period of time. Thus, the compositions and the agents of the present invention are beneficial as foods and drinks that can be continuously consumed on a daily basis by, for example, infants, elders, sick persons, and convalescent persons.

DETAILED DESCRIPTION OF THE INVENTION

Figure 1:
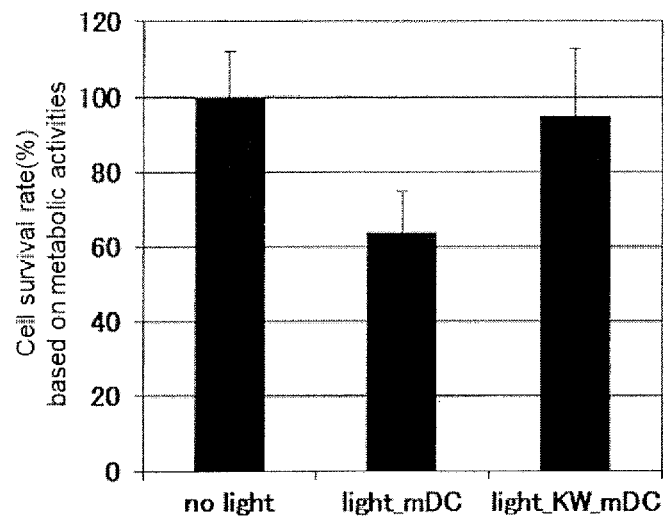
FIG. 1A is a figure showing the effect of the supernatant from a human mDC (myeloid dendritic cell) culture stimulated with *Lactobacillus paracasei* KW3110 to suppress cell death induced by exposure to blue light in human retinal pigment epithelial cells (evaluation based on metabolic activities).
FIG. 1B is a figure confirming the effect of *Lactobacillus paracasei* on human retinal pigment epithelial cells under blue light exposure (evaluation based on metabolic activities).
Figure 1:
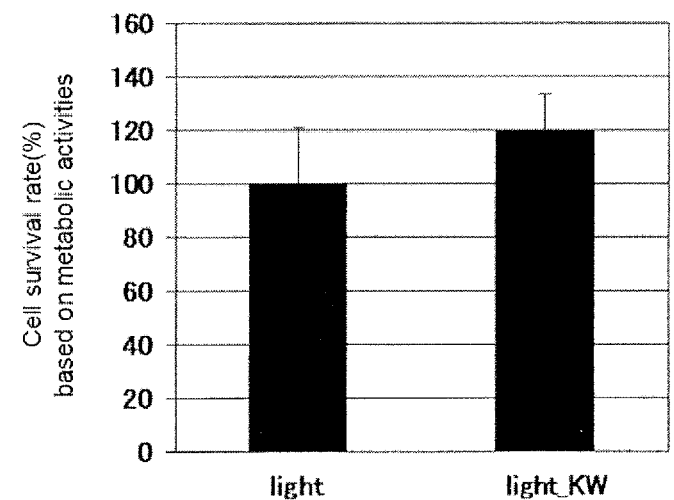

Now, the present invention will be described in detail.

According to the first aspect of the present invention, a composition and an agent for use in suppressing or improving conditions caused by retinal inflammation resulting from light damage are provided, each of which comprises a lactic acid bacterium as an active ingredient.

The phrase "retinal inflammation resulting from light damage" as used in the present invention refers to retinal inflammation caused by disorders resulting from exposure of the retina to light, particularly retinal inflammation caused by exposure of the retina to particular wavelengths of light. The term "particular wavelengths of light" refers to light with wavelengths of 10 to 830 nm, particularly so-called blue light. Blue light refers to light with wavelengths of 380 to 530 nm, particularly light with wavelengths of 380 to 495 nm, which is mainly emitted from, for example, IT devices such as personal computers and smartphones.

The phrase "conditions caused by retinal inflammation resulting from light damage" as used in the present invention includes conditions resulting from development of various eye diseases, and discomfort in eyes (oculi), though the latter is not a disease. In the present invention, terms "eye" and "oculus" are synonymous and can be used interchangeably.

The term "eye discomfort" as used herein includes objectively or subjectively perceived eye fatigue and dry eye. More specifically, these conditions may be sometimes objectively expressed as numerical values, such as refractivity value, visual acuity value, flicker value (an indicator of eye fatigue), range of accommodation (relating to focus adjustment), amount of tear secretion, and contrast sensitivity value. Additionally, the subjectively perceived eye fatigue may involve not only ocular sensations but also those perceived by body parts other than eyes, such as, for example, ocular pain, blurred vision, excess tearing, stiffness of the shoulder or lower back, ocular fatigue sensation, flickering vision, double vision, frustration, stuffy head (dull headache), headache, gritty eye sensation (foreign body sensation), heavy eyelids, eye redness, difficulty in keeping eyes open, blurred vision caused by using eyes, dazzled vision, deterioration of eye conditions during reading, for example, newspapers, magazines, or books, poor concentration due to eye conditions, troubles with business, housework, and study due to eye conditions, a tendency to abandon a desire to go out due to eye conditions, and bad feeling due to eye conditions. The dry eye may involve not only ocular sensations but also those perceived by body parts other than eyes, such as, for example, gritty eye sensation (foreign body sensation), dry eye sensation, ocular pain, ocular fatigue sensation, heavy eyelids, eye redness, difficulty in keeping eyes open, blurred vision caused by using eyes, dazzled vision, deterioration of eye conditions during reading, for example, newspapers, magazines, or books, poor concentration due to eye conditions, troubles with business, housework, and study due to eye conditions, a tendency to abandon a desire to go out due to eye conditions, and bad feeling due to eye conditions.

Examples of a quantifiable conditions caused by retinal inflammation resulting from light damage include cell death of retinal pigment epithelial cells and decrease in retinal outer nuclear layer thickness.

The phrase "suppression of conditions caused by retinal inflammation resulting from light damage" as used in the present invention means suppressing deterioration or manifestation of such conditions and is used inclusively to mean a preventative or prophylactic action against such conditions. The phrase "improvement of conditions caused by retinal inflammation resulting from light damage" as used in the present invention is used inclusively to mean relief of such conditions or recovery from such conditions.

According to the second aspect of the present invention, a composition and an agent for use in suppressing or improving eye fatigue are provided, each of which comprises a lactic acid bacterium as an active ingredient.

The term "eye fatigue" as used in the present invention means a type of eye fatigue that is induced by foreign stimuli. The eye fatigue includes, for example, the aforementioned conditions illustrated as examples of the eye discomfort (particularly, ocular fatigue sensation, blurred vision, stiffness of the shoulder or lower back, dull headache). Additionally, eye fatigue caused by VDT work is regarded as a typical example of the "eye fatigue." The "eye fatigue" includes simple eye fatigue, namely physiological fatigue in eyes, and pathological fatigue in eyes that is perceived as an uncomfortable tired feeling and is only insufficiently resolved even after a period of rest. The pathological fatigue in eyes may be clinically considered as asthenopia, but the terms "eye fatigue" and "asthenopia" are generally used synonymously (see Nanzando's Medical Dictionary, Nanzando Co., Ltd.). In the present invention, the term "eye fatigue" is thus to be used inclusively to mean "asthenopia."

Examples of the foreign stimuli capable of inducing eye fatigue include light stimulation and also a kind of light damage that induces the aforementioned retinal inflammation. Examples of the light causing the light stimulation and the light damage capable of inducing eye fatigue include light with wavelengths of 10 to 830 nm, while examples of the light which is particularly capable of inducing eye fatigue include light with wavelengths of 380 to 530 nm (more specifically, 380 to 495 nm), namely blue light.

The phrase "suppression of eye fatigue" as used in the present invention means suppressing deterioration or manifestation of eye fatigue and is used inclusively to mean a preventative or prophylactic action against eye fatigue. The phrase "improvement of eye fatigue" as used in the present invention means improving eye fatigue and is used inclusively to mean relief of eye fatigue or recovery from eye fatigue.

According to the third aspect of the present invention, a composition and an agent for use in suppressing cell death of retinal pigment epithelial cells or decrease in retinal thickness, or for use in protecting visual functions under visible light are provided, each of which comprises a lactic acid bacterium as an active ingredient.

Cell death of retinal pigment epithelial cells and decrease in retinal thickness can be induced by light stimulation or light damage and can be suppressed by the composition and the agent of the present invention. The light causing the light stimulation and the light damage refers to the same light as described above.

Examples of the lactic acid bacterium used as an active ingredient in the present invention include bacteria classified into the following genus, species, and strains. The term "lactic acid bacteria" means bacteria capable of producing lactic acid and includes bacteria of Lactic acid *bacillus* and Lactic acid cocci. Specifically, lactic acid bacteria can be isolated and identified by methods known to those skilled in the art (see, for example, Japan Society for Lactic Acid Bacteria ed., "Science and Technology of Lactic Acid Bacteria").

Genus *Lactobacillus*: *L. delbrueckii*, *L. acidophilus*, *L. casei*, *L. fructivorans*, *L. hilgardii*, *L. paracasei*, *L. rhamnosus*, *L. plantarum*;
Genus *Bifidobacterium*: *B. bifidum*, *B. adolescentis*;
Genus *Enterococcus*: *E. faecalis*, *E. faecium*;
Genus *Lactococcus*: *L. lactis*, *L. cremoris*;
Genus *Pediococcus*: *P. damnosus*;
Genus *Streptococcus*: *S. salivarius*;
Genus *Leuconostoc*: *L. mesenteroides*.

Among those, bacteria classified into the genus *Lactobacillus*, particularly *Lactobacillus paracasei*, are especially preferable. Specific examples of *Lactobacillus paracasei* strain include *Lactobacillus paracasei* strain KW3110.

*Lactobacillus paracasei* strain KW3110 is available as *L. casei* strain L14 from the Japan Dairy Technical Association.

The strain L14 is described to be a strain of *L. casei* according to the description by the Japan Dairy Technical Association. However, the inventors analyzed the strain by RFLP (Restriction Fragment Length Polymorphism) and AFLP (Amplified Fragment Length Polymorphism) using Qualicon RiboPrinter system and determined that the strain was a strain of *L. paracasei*. Thus, the strain is described in the present invention as a strain of *Lactobacillus paracasei*. *Lactobacillus paracasei* KW3110 is available from the Japan Dairy Technical Association, as described above, and is furthermore deposited under Accession No. PERM BP-08634 (date of deposit: Feb. 20, 2004) to the International Patent Organism Depositary, National Institute of Advanced Industrial Science and Technology (Chuo #6, 1-1-1, Higashi, Tsukuba-shi, Ibaraki 305-8566, Japan; currently International Patent Organism Depositary, Biotechnology Center, National Institute of Technology and Evaluation (KITE-IPOD), #120, 2-5-8, Kazusa-kamatari, Kisarazu-shi, Chiba 292-0818, Japan), which is an international depositary authority under the Budapest Treaty on the International Recognition of the Deposit of Microorganisms for the Purposes of Patent Procedure. Additionally, a derivative of *Lactobacillus paracasei* KW3110 is deposited under Accession No. FERM BP-08635 to the same International Patent Organism Depositary.

Furthermore, the lactic acid bacterium used as an active ingredient in the present invention is preferred to have an effect to suppress or improve conditions caused by retinal inflammation resulting from light damage in biological bodies where the lactic acid bacterium is orally ingested. The lactic acid bacterium used as an active ingredient in the present invention can reach the intestinal tract while keeping structures at such a level that, for example, live cells, or dead cells or components thereof (for example, cell membrane, components of cell membrane, nucleus, nucleic acids constituting nuclear components) of the lactic acid bacterium can exert their effects on immune cells present in the intestinal tract.

Furthermore, bacteria of any strain comparable to those of the above-described strain can be used in the present invention. The comparable strain as used herein refers to a bacterial strain originated (derived) from the above-described strain or the parental strain of the above-described strain or a progeny strain of the parental strain.

The phrase "lactic acid bacterium used as an active ingredient in the present invention" includes cultures of the lactic acid bacterium. The term "culture" includes, for example, live bacterial cells, dead bacterial cells, a homogenate of live or dead bacterial cells, a lyophilizate of live or dead bacterial cells, a homogenate of the lyophilizate, enzyme-treated live or dead bacterial cells, culture liquid, and culture liquid extract, and also includes fractions of the lactic acid bacterium and processed products of the lactic acid bacterium. The dead bacterial cells can be obtained, for example, by heat treatment, treatment with drugs such as antibiotics, treatment with chemicals such as formalin, UV treatment, or radiation treatment such as treatment with gamma rays. Furthermore, a DNA or RNA fraction of the above-described lactic acid bacterium is included in the cultures of the lactic acid bacterium. The processed product includes, for example, heat-treated bacterial cells (dead bacterial cells), a lyophilizate of the heat-treated bacterial cells, and a culture containing the heat-treated bacterial cells, and further includes a bacterial homogenate prepared, for example, by sonication and an enzyme-treated bacterial solution. Additionally, the processed product includes, for example, a product prepared by removing cell walls from bacterial cells by an enzymatic or mechanical measure, and furthermore also includes a nucleic acid-containing fraction prepared by dissolving bacterial cells with, for example, a surfactant and then precipitating the fraction with, for example, ethanol. Furthermore, the bacterial cells may include dead cells.

The lactic acid bacterium can be cultured using a known culture medium by a known method. M.R.S. medium, GAM medium, and LM17 medium can be used as the culture medium, to which inorganic salts, vitamins, amino acids, antibiotics, serum, and the like may be added as appropriate. The culture may be continued at 25 to 40° C. for several hours to several days.

After culture, cells of the lactic acid bacterium are collected by centrifugation or filtration. In cases where dead cells of the lactic acid bacterium are used, the lactic acid bacterium may be killed and inactivated by, for example, autoclaving.

A lactic acid bacterium used as an active ingredient in the present invention can be screened by the following method. That is, bacteria of each candidate strain are cultured. Immune cells are co-cultured in the presence of the culture and the supernatant is then recovered from the immune cell culture. Retinal pigment epithelial cells are cultured in the presence of the collected immune cell culture supernatant. The culture is performed with or without light (preferably blue light) exposure. Cell death is induced in retinal pigment epithelial cells when those cells are cultured under light (preferably blue light) exposure. However, cell death of retinal pigment epithelial cells is suppressed when those cells are cultured in the presence of the culture supernatant from immune cells co-cultured with the lactic acid bacterium that can suppress or improve conditions caused by retinal inflammation resulting from light damage. Accordingly, a lactic acid bacterium used as an active ingredient in the present invention (particularly, a lactic acid bacterium that can suppress or improve conditions caused by retinal inflammation resulting from light damage) can be selected on the basis of whether or not cell death of the retinal pigment epithelial cells induced by light (preferably blue light) can be suppressed by the culture supernatant from the immune cells co-cultured with the bacteria of the candidate strain. That is, the present invention provides a method of screening lactic acid bacterial strains that can suppress or improve conditions caused by retinal inflammation resulting from light damage, wherein the method comprises the steps of culturing immune cells in the presence of a lactic acid bacterial culture of each candidate strain, and culturing retinal pigment epithelial cells under light exposure in the presence of the supernatant of the obtained immune cell culture. Examples of the immune cells used for the screening preferably include dendritic cells, monocytes, and macrophages, more preferably myeloid dendritic cells and macrophages, and particularly preferably myeloid dendritic cells.

The composition and the agent of the present invention can be administered or fed to animals such as human (preferably mammals including a human) to exert the effects thereof. For example, the composition and the agent of the present invention for use in suppressing or improving conditions caused by retinal inflammation resulting from light damage can be administered or fed to suppress cell death induced by light damage in retinal pigment epithelial cells. Additionally, the composition and the agent of the present invention for use in suppressing or improving conditions caused by retinal inflammation resulting from light damage can be administered or fed to suppress light damage-induced decrease in retinal outer nuclear layer thickness, so that the retinal outer nuclear layer thickness can be maintained.

The composition and the agent of the present invention for use in suppressing or improving conditions caused by retinal inflammation resulting from light damage can act on, for example, myeloid dendritic cells (mDCs) and can suppress cell death of retinal pigment epithelial cells induced by light damage via the mDCs.

The composition and the agent of the present invention exert their effects not only on a human but also on farm animals, such as cow, horse, sheep, and pig, and additionally on pet animals, such as dog and cat.

The composition and the agent of the present invention can be provided in the form of, for example, pharmaceutical products, quasi-drugs, food products, and feed products (including pet foods). That is, the composition and the agent of the present invention include pharmaceutical compositions. The composition and the agent of the present invention can be orally administered. Dosage forms suitable for oral administration include granules, powders, tablets (including sugar-coated tablets), pills, capsules, syrups, emulsions, and suspensions. These formulations can be formulated with pharmaceutically acceptable carriers, according to procedures commonly used in the art. Examples of the pharmaceutically acceptable carriers include, for example, excipients, binders, diluents, additives, flavoring agents, buffers, thickeners, coloring agents, stabilizing agents, emulsifiers, dispersing agents, suspending agents, and preservatives.

Furthermore, the composition and the agent of the present invention include food compositions, namely food or beverage products. Such a food composition can be used for prevention, suppression, or improvement of discomfort in eyes (oculi). The types of the targeted food or beverage products are not limited to particular types as long as the effects of active ingredients of the composition and the agent of the present invention (particularly, effects to suppress or improve conditions caused by retinal inflammation resulting from light damage) are not reduced. Examples of the food or beverage product include dairy products, such as yogurt, processed milk, cheese, and milk-containing sweets; beverages, such as soft drinks, non-alcoholic drinks, sports drinks, and energy drinks; cakes, such as chocolates and biscuits (cookies); breads; dressings; and sauces such as pasta sauces. Additionally, the food composition includes supplements (dietary supplements). The dosage forms of the supplements are not limited, and a dosage form like a drug delivery system may be of course employed. In addition, these food compositions may contain other functional ingredients.

The food or beverage product of the present invention include, for example, foods with function claims, health food or beverage products, food or beverage products for specified health uses, food or beverage products with nutrient function claims, health-promoting food or beverage products, and foods for diseased people. The food or beverage products for specified health uses as used herein refer to food or beverage products that are permitted to indicate that specific health functions can be expected from intake of the food or beverage products with the intention of achieving those health functions in daily eating habits. Moreover, the foods with function claims as used herein refer to foods that are approved by the Consumer Affairs Agency, Japan to indicate expected effects for health on their packages under the responsibility of business operators and on the basis of scientific evidence.

Examples of the claims for those food or beverage products include, but are not limited to, the following claims.

Because the food or beverage product of the present invention is one embodiment of the composition and the agent of the present invention, the package label of the food or beverage product may indicate the intended use of the composition and the agent of the present invention. In this case, the label of the food or beverage product of the present invention may contain some or all of the following claims for users' easy understanding:

"To lighten eye fatigue from, for example, personal computer use,"

"To lighten eye fatigue,"

"To protect eyes from stimulation by light such as blue light,"

"To protect eyes stimulated by light and adjust eye conditions,"

"To maintain, improve, support, normalize, and help in maintaining visual functions against stimulation by light such as blue light, and to reduce visual dysfunction,"

"To alleviate, reduce and prevent eye fatigue due to stimulation by light such as blue light,"

"To alleviate and relieve eye fatigue due to stimulation by light such as blue light, and to protect eyes from eye fatigue and blurred vision,"

"To alleviate, reduce, and prevent stiffness of the shoulder or lower back resulting from eye fatigue caused by stimulation by light such as blue light,"

"To maintain, improve, support, and normalize the eye's moisture against stimulation by light such as blue light,"

"To alleviate, reduce, and prevent dry eye due to stimulation by light such as blue light,"

"To alleviate dry eye due to stimulation by light such as blue light, and to maintain, improve, support, and normalize visual functions,"

"To maintain, improve, support, and normalize the accommodation ability that may be decreased by stimulation by light such as blue light,"

"To maintain, improve, support, and normalize the contrast sensitivity that may be decreased by stimulation by light such as blue light,"

"To prevent presbyopia induced by excess use of smartphone,"

"For the countermeasure against presbyopia induced by excess use of smartphone,"

"To modulate eye conditions that may be deteriorated by stimulation by light such as blue light."

The ingestion amount of the food composition of the present invention is normally from 1 to 1000 mg/day/person, preferably 10 to 500 mg/day/person, more preferably from 25 to 100 mg/day/person, on the dry mass basis of lactic acid bacteria and can be appropriately varied. The ingestion period is normally 1 day or longer, preferably 3 days or longer, and more preferably 1 week or longer.

The food composition of the present invention can suppress or improve eye fatigue, as well as can prevent, suppress, or improve any subjectively or objectively perceived eye discomfort during the period from the onset of ingestion to the assay time points.

Additionally, eye fatigue that can be induced by stimulation with light, such as blue light, for a certain period of time can be suppressed or improved, as well as discomfort that can result from stimulation with light, such as blue light, for a certain period of time can be prevented by the food composition of the present invention at an arbitrary time point following the onset of the ingestion period. Furthermore, even if such eye discomfort as resulting from light damage or such eye fatigue as resulting from light damage is noticed before the stimulation with light under the same conditions as above, an increase of eye discomfort or eye fatigue after the light stimulation compared with that before the light stimulation can be prevented, suppressed, or improved by the food composition of the present invention.

According to another aspect of the present invention, a method of suppressing or improving eye fatigue is provided, which comprises feeding or administering an effective amount of a lactic acid bacterium to a mammal, including a human. The present invention also provides a method of suppressing or improving conditions caused by retinal inflammation resulting from light damage, which comprises feeding or administering an effective amount of a lactic acid bacterium to a mammal, including a human. The present invention also provides methods of suppressing cell death of retinal pigment epithelial cells or decrease in retinal thickness and of protecting visual functions under visible light, which comprise feeding or administering an effective amount of a lactic acid bacterium to a mammal, including a human. The methods of the present invention can be practiced according to the description on the composition and the agent of the present invention.

The methods of the present invention may be used in mammals including a human, and both therapeutic and non-therapeutic uses are contemplated. In this specification, the term "non-therapeutic" means excluding the act of performing surgery on, treating, or diagnosing a human (i.e., medical practices on humans), specifically, excluding a procedure in which a physician or an individual who is directed by a physician performs surgery on, treats, or diagnoses a human.

According to still another aspect of the present invention, provided are use of a lactic acid bacterium for the manufacture of an agent for suppressing or improving eye fatigue and use of a lactic acid bacterium as an agent for suppressing or improving eye fatigue. The present invention also provides use of a lactic acid bacterium for the manufacture of an agent for suppressing or improving conditions caused by retinal inflammation resulting from light damage, and use of a lactic acid bacterium as an agent for suppressing or improving conditions caused by retinal inflammation resulting from light damage. The present invention further provides use of a lactic acid bacterium for the manufacture of an agent for suppressing cell death of retinal pigment epithelial cells or decrease in retinal thickness or an agent for protecting visual functions under visible light, and use of a lactic acid bacterium as an agent for suppressing cell death of retinal pigment epithelial cells or decrease in retinal thickness or an agent for protecting visual functions under visible light. The use of the present invention can be practiced according to the description on the composition and the agent of the present invention.

According to yet still another aspect of the present invention, a lactic acid bacterium is provided, which is for use in suppressing or improving eye fatigue, for use in suppressing or improving conditions caused by retinal inflammation resulting from light damage, for use in suppressing cell death of retinal pigment epithelial cells or decrease in retinal thickness, and for use in protecting visual functions under visible light. The above-described lactic acid bacterium can be practiced according to the description on the composition and the agent of the present invention.

The present invention also provides the following inventions.

[101] A food composition comprising a lactic acid bacterium for use in preventing or improving conditions caused by retinal inflammation resulting from light damage.
[102] The food composition according to [101], wherein said light has a wavelength of 380 nm to 530 nm.
[103] The food composition according to [101] or [102], wherein said lactic acid bacterium is a bacterium belonging to the genus *Lactobacillus*.
[104] The food composition according to any of [101] to [103], wherein said lactic acid bacterium is *Lactobacillus paracasei*.
[105] The food composition according to any of [101] to [104], wherein said lactic acid bacterium is *Lactobacillus paracasei* strain KW3110.
[106] The food composition according to any of [101] to [105], wherein said condition caused by retinal inflammation resulting from light damage is eye discomfort.
[107] The food composition according to [106], wherein said eye discomfort is objectively or subjectively perceived eye fatigue, or dry eye.
[108] The food composition according to any of [101] to [107], wherein said food composition is in the form of a supplement.

EXAMPLES

Now, the present invention will be specifically described by way of Examples below, but the present invention is not limited by those Examples.

[Example 1] Preparation of Bacteria of a Lactic Acid Bacterial Strain

<Experimental Method>

The lactic acid bacterium (*Lactobacillus paracasei* KW3110) used in Examples of the present invention was obtained from the Japan Dairy Technical Association. The lactic acid bacterium was cultured using M.R.S. (de Man, Rogosa, Sharpe) medium (OXOID) at 37° C. for 48 hours. Bacterial cells were collected and then washed with sterilized water three times, and killed by autoclaving at 100° C. for 30 minutes. Subsequently, the bacterial cells were lyophilized and dissolved in PBS (manufactured by Takara Bio Inc.) to a concentration of 1 mg/mL.

[Example 2] Evaluation of the Effect of the Culture Supernatant from Human mDCs (Myeloid Dendritic Cells) with KW3110 Stimulation to Suppress Cell Death of Human Retinal Pigment Epithelial Cells Induced by Exposure to Blue Light The culture supernatant from human mDCs stimulated with *Lactobacillus paracasei* strain KW3110 was examined for its ability to suppress cell death induced by exposure to blue light in human retinal pigment epithelial cells.
<Experimental Methods>
(1) Preparation of an mDC Culture Supernatant
CD14$^+$ mononuclear cells were isolated using a Monocyte isolation kit (manufactured by Milteny Biotec K.K.) from human peripheral blood mononuclear cells (manufactured by PromoCell GmbH) and then suspended at a concentration of $1.0 \times 10^6$ cells/mL in RPMI1640 (manufactured by Sigma-Aldrich Co. LLC.) containing 10% FBS (manufactured by Moregate Biotech)+1% P/S (manufactured by Invitrogen)+ 50 µM 2-mercaptoethanol (manufactured by Invitrogen) supplemented with recombinant human-GM-CSF (manufactured by R&D Systems, Inc.) and recombinant human- IL-4 (manufactured by R&D Systems, Inc.) at concentrations of 50 ng/mL and 100 ng/mL, respectively. An aliquot of 2 mL from the suspension was added to each well of a 6-well flat bottom plate (manufactured by Iwaki) and incubated at 37° C. in 5% $CO_2$ or 6 days to induce human myeloid dendritic cells (mDCs). Subsequently, those cells were collected and then incubated an aliquot of 500 μL at a concentration of $0.6\times10^5$ cells/mL using a 48-well plate. The KW3110 strain was then added to the mDC culture at a concentration of 10 μg/mL and cultured for 24 hours, and the culture supernatant was then collected.

(2) Preparation of Human Retinal Epithelial Cells

Human retinal pigment epithelial cells (ARPE19; purchased from ATCC) were cultured at 37° C. in 5% $CO_2$ for 72 hours in DMEM/F12 (manufactured by Thermo Fisher Scientific Inc.) medium containing 10% FBS (manufactured by Moregate Biotech)+1% P/S (manufactured by Invitrogen) using a 96-well plate at a density of $3.0\times10^3$ cells/well. After cultivation, the culture medium was replaced with DMEM/F12 (manufactured by Thermo Fisher Scientific Inc.) containing 1% FBS (manufactured by Moregate Biotech)+1% P/S (manufactured by Invitrogen) and further incubated for 24 hours.

(3) Blue Light Irradiation Test

The culture supernatant recovered in the above (1) from human mDCs with stimulation by the KW3110 strain was added 1/100 (vol/vol) and then incubated for 6 hours. The cultured cells were exposed to blue light (with a wavelength 470 nm; manufactured by Optocode Corporation) at an illuminance of 2000 lux for 30 minutes. Control experiments were performed under a condition where no blue light exposure was performed and the supernatant from a human mDC culture without stimulation by the KW3110 strain was used and under a condition where the blue light exposure was performed and the supernatant from the human mDC culture without stimulation by the KW3110 strain was used. All the experiments were triplicated, and cell viabilities (cell survival rates based on metabolic activities) were measured using a Cell counting kit-8 (manufactured by Dojindo Laboratories) 24 hours after light exposure.

(4) Evaluation of the Effect of the Supernatant from the Culture Stimulated with the KW3110 Strain The potential of the KW3110 strain itself used in the experiments from the above (1) to (3) to prevent cell death of retinal epithelial cells was evaluated. That is, cell viability (cell survival rate based on metabolic activities) was measured in a sample (light KW) of human retinal epithelial cells prepared in (2) with addition of the KW3110 strain suspended in PBS and exposure to blue light under the same conditions as in (3) and in a sample (light) of human retinal epithelial cells prepared in (2) with direct exposure to blue light.

<Results>

The results of the assay of cell viability (cell survival rate) are shown in FIG. 1A; the bar above "no light" represents the result obtained under the condition where no blue light exposure was performed and the supernatant from the human mDC culture without stimulation by the KW3110 strain was used; the bar above "light_mDC" represents the result obtained under the condition where the blue light exposure was performed and the culture supernatant without stimulation by the KW3110 strain was used; the bar above "light_KW_mDC" represents the result obtained under the condition where the blue light exposure was performed and the supernatant from the human mDC culture with stimulation by the KW3110 strain was used. The blue light exposure induced cell death of the human retinal pigment epithelial cells, but a decrease of cell survival rate was not observed even under the blue light irradiation condition when the human retinal pigment epithelial cells were irradiated in the presence of the supernatant from the human mDC culture with stimulation by the KW3110 strain.

The result of identifying the effect of the KW3110 strain is shown in FIG. 1B. The bar above "light_KW" represents the result obtained under the condition where the retinal epithelial cells were irradiated with blue light with addition of the KW3110 strain suspension, and the bar above "light" represents the result obtained under the condition where the retinal epithelial cells were irradiated with blue light without addition of the KW3110 strain suspension. No significant difference was observed between the both groups.

Accordingly, it is indicated that the supernatant from the human mDC culture with stimulation by the KW3110 strain has an effect to suppress cell death of retinal pigment epithelial cells induced by exposure to blue light.

[Example 3] Evaluation of the Effect of the Culture Supernatant from Human M2 Macrophage Cells with KW3110 Stimulation to Suppress Cell Death of Human Retinal Pigment Epithelial Cells Induced by Exposure to Blue Light <Experimental Methods>

(1) Preparation of a Human M2 Macrophage Culture Supernatant $CD14^+$ mononuclear cells were isolated using a Monocyte isolation kit (manufactured by Milteny Biotec K.K.) from human peripheral blood mononuclear cells (manufactured by PromoCell GmbH). The isolated cells were suspended at a concentration of $2\times10^5$ cells/mL using a Human M2 macrophage Differentiation Kit (manufactured by R&D Systems, Inc.), and an aliquot of 500 μL was added to each well of a 48-well plate (manufactured by Iwaki) and incubated at 37° C. in 5% $CO_2$ for 6 days with exchange of the culture medium every 3 days to induce human M2 macrophage cells. The KW3110 strain was then added to the M2 macrophage culture system at a concentration of 10 μg/mL and co-cultured for 24 hours, and the culture supernatant was then collected.

(2) Evaluation of the Effect of the Culture Supernatant

Evaluation Based on Metabolic Activities

Cell viabilities (cell survival rates based on metabolic activities) were calculated and measured using a Cell counting kit-8 (manufactured by Dojindo Laboratories) similarly to Example 2 at a time point of 30 minutes after blue light exposure.

Evaluation Using Dead Cell Staining Regents

The same method as Example 2 was used for the evaluation, except that the length of time for blue light exposure was 50 minutes and the method used to evaluate cell viability (cell survival rate) was a method based on dead cell staining (all cells were stained with a Cellsrain-Hoechst 33342 solution (manufactured by Dojindo Laboratories) and dead cells were stained with a Cellsrain-PI solution (manufactured by Dojindo Laboratories), and a cell survival rate was calculated from the respective numbers of stained cells).

<Results>

Figure 2:
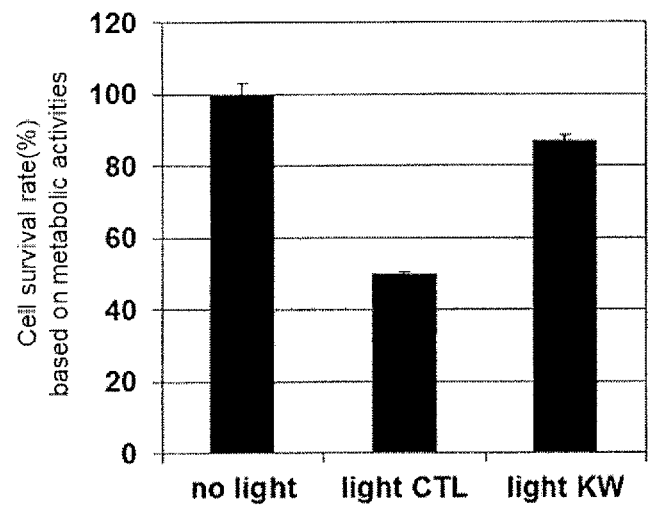
FIG. 2A is a figure showing the effect of the supernatant from a human M2 (macrophage cell) culture stimulated with *Lactobacillus paracasei* KW3110 to suppress cell death induced by exposure to blue light in human retinal pigment epithelial cells (evaluation based on metabolic activities).
FIG. 2B is a figure showing the effect of the supernatant from a human M2 (macrophage cell) culture stimulated with *Lactobacillus paracasei* KW3110 to suppress cell death induced by exposure to blue light in human retinal pigment epithelial cells (evaluation by using dead cell staining regents).
Figure 2:
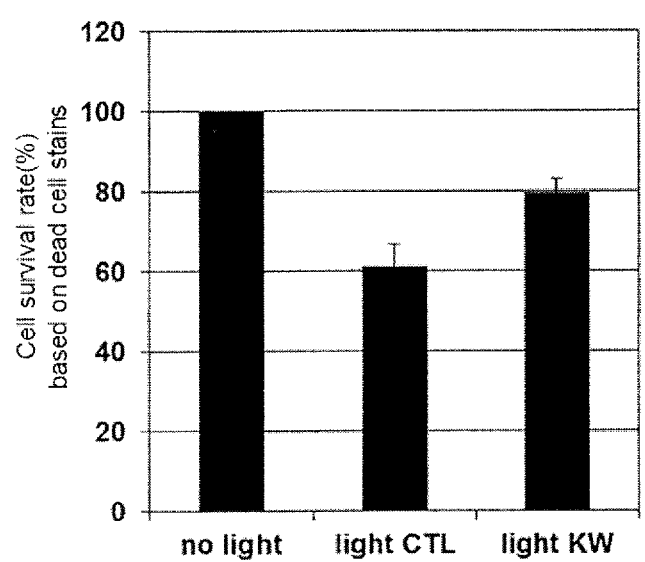

The result of the assay of cell viability (cell survival rates based on metabolic activities) is shown in FIG. 2A, and the result of the assay of cell viability (from the assay using dead cell staining regents) is shown in FIG. 2B. It was found that the blue light exposure induced cell death of the human retinal pigment epithelial cells, and that a decrease of cell survival rate was not observed even under the blue light irradiation condition when the human retinal pigment epithelial cells were irradiated in the presence of the supernatant from the human M2 macrophage culture with stimulation by the KW3110 strain. Accordingly, it is indicated that the supernatant from the human M2 macrophage culture with stimulation by the KW3110 strain has an effect to suppress cell death induced by exposure to blue light in retinal pigment epithelial cells.

Figure 3:
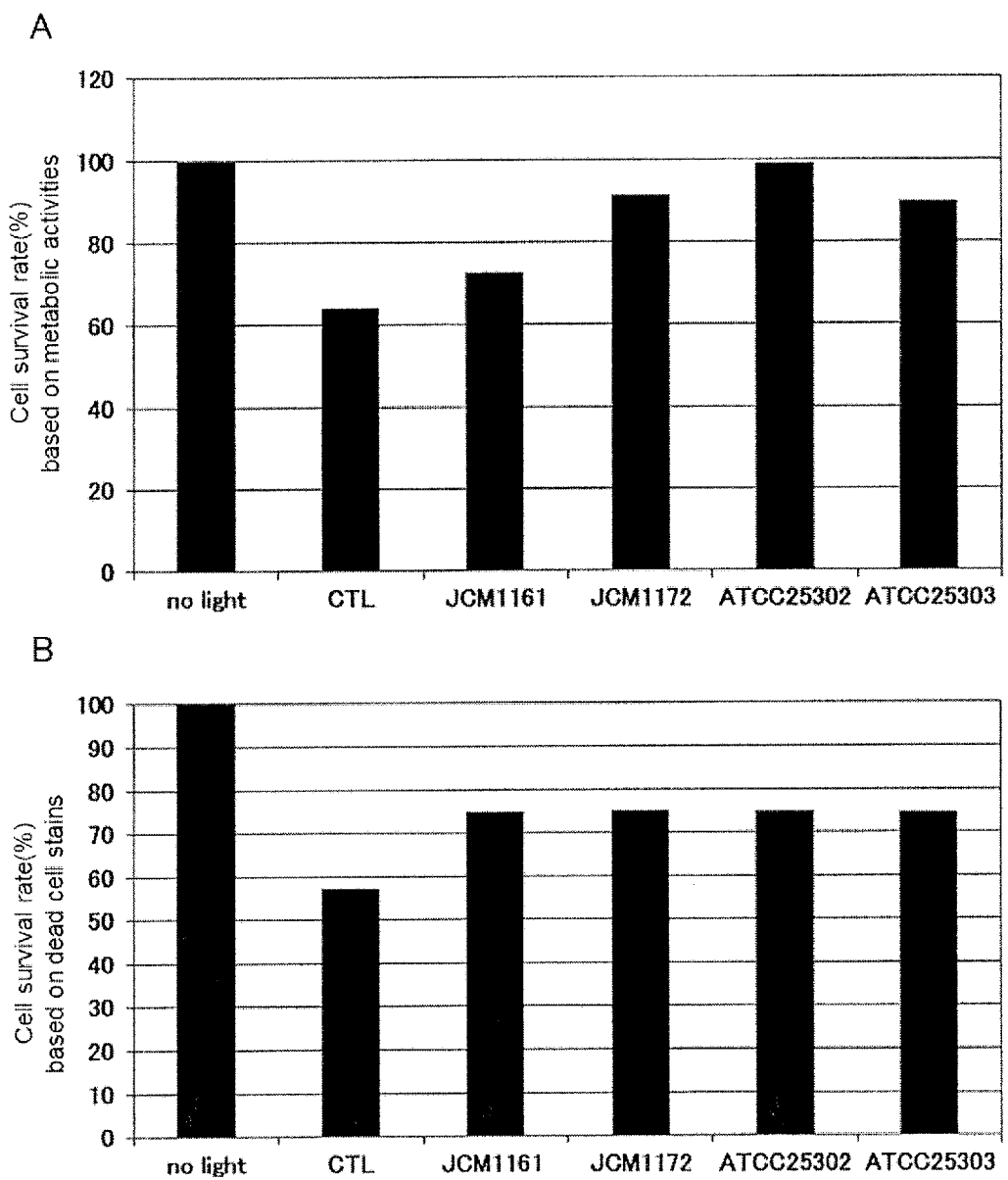
FIG. 3A is a figure showing the effect of the supernatants from human M2 macrophage cell cultures stimulated with each of four strains belonging to *Lactobacillus paracasei* (JCM1161, JCM1172, ATCC25302, ATCC25303) to suppress cell death induced by exposure to blue light in human retinal pigment epithelial cells (evaluation based on metabolic activities).
FIG. 3B is a figure showing the effect of the supernatants from human M2 macrophage cell cultures stimulated with each of four strains belonging to *Lactobacillus paracasei* (JCM1161, JCM1172, ATCC25302, ATCC25303) to suppress cell death induced by exposure to blue light in human retinal pigment epithelial cells (evaluation by using dead cell staining regents).

[Example 4] Evaluation of the Effect of the Culture Supernatant from Human M2 Macrophage Cells Stimulated with Lactic Acid Bacteria of Strains Other than KW3110 to Suppress Cell Death of Human Retinal Pigment Epithelial Cells Induced by Exposure to Blue Light The culture supernatants from human mDCs stimulated with each of four strains belonging to *Lactobacillus paracasei* (JCM1161, JCM1172, ATCC25302, and ATCC25303) were examined for their ability to suppress cell death of human retinal pigment epithelial cells induced by exposure to blue light.
<Experimental Method>
Cell viabilities (cell survival rates) were measured by the assay based on metabolic activities (blue light exposure time: 30 minutes; a Cell counting kit-8 (the same as described above) was used) and the assay using dead cell staining regents (blue light exposure time: 50 minutes; a Cellstain-Hoechst 33342 solution, Cellstain-PI solution (the same as described above) was used).
<Results>
The result of the assay of cell viability (cell survival rates based on metabolic activities) is shown in FIG. 3A, and the result of the assay of cell viability (from the assay for cell survival rate using dead cell staining regents) is shown in FIG. 3B. The effect to suppress cell death was confirmed also in the four strains belonging to *Lactobacillus paracasei*.
<Conclusion>
The results from Examples 2, 3, and 4 indicated that the culture supernatant from human immune cells (mDCs or macrophage cells) stimulated with bacteria of any of the five strains belonging to *Lactobacillus paracasei* has an effect to suppress cell death of retinal pigment epithelial cells induced by exposure to blue light. This result suggested the possibility that bacteria of any strain belonging to *Lactobacillus paracasei* potentially has the same effect.

[Example 5] Effect of Ingestion of the KW3110 Strain in Blue Light-Exposed Animal Models The lactic acid bacterium specified in the present invention is expected to be consumed not only by healthy individuals but particularly by individuals who look at the screen of, for example, a personal computer or smartphone for hours. Thus, the effect of ingesting the KW3110 strain was studied in blue light-exposed animal models.
<Experimental Method>
BALB/c mice (5-week-old males, purchased from Charles River Laboratories Japan, Inc.) were divided into four groups of 6 mice: mice group fed a standard diet (AIN93G; manufactured by Oriental Yeast Co., Ltd.) without blue light exposure (no light CTL), mice group fed a KW3110 strain-containing diet (containing 250 mg of the KW3110 strain (the same as prepared in Example 1) in 1 kg of the standard diet on dry weight basis) without blue light exposure (no light KW), mice group fed a standard diet (AIN93G; manufactured by Oriental Yeast Co., Ltd.) with blue light exposure (light CTL), and mice group fed a KW3110 strain-containing diet with blue light exposure (light KW). The mice had ad libitum access to water and the diet. Treatments to the mice in the respective groups are as shown in Table 1. The arrows in Table 1 indicate dates on which the treatments were performed.

The period of KW3110 strain ingestion was 2 weeks, and the daily ingestion amount of the KW3110 strain bacteria was about 1 mg. The administration of the KW3110 strain bacteria was started on Day -14, and blue light exposure (with 470 nm at 3000 lux for 3 hours) was performed on Days 0, 1, and 2. For the blue light exposure, light sources were located on the two opposite walls of each rearing cage, and the light intensity was adjusted to give a value of 3000 lux when the illuminance was measured at the center of the floor.

Figure 4:
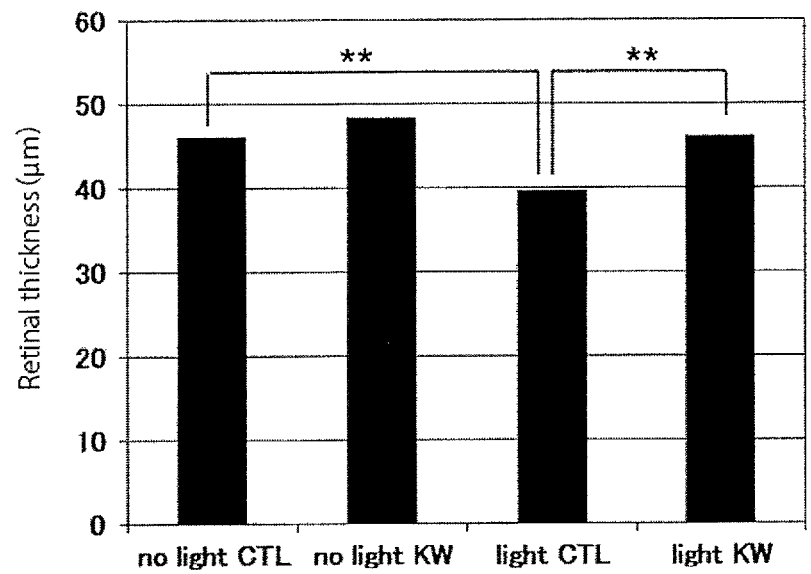
FIG. 4 is a figure showing the retinal outer nuclear layer thickness (retinal thickness) measured using blue light-exposed animal models.

Dissection was performed on Day 3, and retinal sections were prepared, stained with hematoxylin and eosin, and then measured for retinal outer nuclear layer thickness. The retina was divided to regions based on the distance from the optic disc, and the retinal outer nuclear layer thickness was measured at seven different positions in each of the regions, and the average of the measured thickness values was determined to be the outer nuclear layer thickness of the region. The thickness of the same retinal region from each individual mouse was used for evaluation between the groups. The statistical evaluation was performed by t-test, and the asterisk (**) in FIG. 4 represents a level of significance of $P<0.01$.[0075]

TABLE 1

| | | -14 | -13 | -12 | -11 | -10 | -9 | -8 | -7 | -6 | -5 | -4 | -3 | -2 | -1 | 0 | 1 | 2 | 3 |
|---|---|---|---|---|---|---|---|---|---|---|---|---|---|---|---|---|---|---|---|
| no light ctrl | KW ingestion | | | | | | | | | | | | | | | | | | |
| | Irradiation | | | | | | | | | | | | | | | | | | |
| | Dissection | | | | | | | | | | | | | | | | | | ↓ |
| no light KW | KW ingestion | ↓ | ↓ | ↓ | ↓ | ↓ | ↓ | ↓ | ↓ | ↓ | ↓ | ↓ | ↓ | ↓ | ↓ | ↓ | ↓ | ↓ | |
| | Irradiation | | | | | | | | | | | | | | | | | | |
| | Dissection | | | | | | | | | | | | | | | | | | ↓ |
| light ctrl | KW ingestion | | | | | | | | | | | | | | | | | | |
| | Irradiation | | | | | | | | | | | | | | | ↓ | ↓ | ↓ | |
| | Dissection | | | | | | | | | | | | | | | | | | ↓ |
| light KW | KW ingestion | ↓ | ↓ | ↓ | ↓ | ↓ | ↓ | ↓ | ↓ | ↓ | ↓ | ↓ | ↓ | ↓ | ↓ | ↓ | ↓ | ↓ | |
| | Irradiation | | | | | | | | | | | | | | | ↓ | ↓ | ↓ | |
| | Dissection | | | | | | | | | | | | | | | | | | ↓ |

<Result>

FIG. 4 shows the retinal outer nuclear layer thickness (retinal thickness) measured using blue light-exposed models. No difference in retinal thickness was observed between the standard diet group (no light CTL) and the mice group fed a standard diet containing KW3110 strain (no light KW) under no blue light exposure condition. A significant decrease in retinal thickness was observed in the standard diet group with blue light exposure (light CTL), as compared to the standard diet group without blue light exposure (no light CTL). The decrease in retinal thickness was considered to result from cell death induced by blue light exposure in the retina. Interestingly, on the contrary, the retinal thickness was kept thick in the KW3110 strain feeding group with blue light exposure (light KW) significantly as compared to the standard diet group with blue light exposure (light CTL). This result suggested that ingestion of the KW3110 strain works to suppress cell death of the retina induced by blue light emitted from personal computers and smartphones, and greatly contributes to preventing retinal damage associated with an excessive amount of VDT (Visual Display Terminal) work with, for example, personal computers.

[Example 6] Effect of Ingestion of the KW3110 Strain in Animal Models Kept Under Normal Visible Light The lactic acid bacterium specified in the present invention was expected to have an effect to protect visual functions under normal visible light, which was thus studied.

<Experimental Method>

BALB/c mice (5-week-old males, purchased from Charles River Laboratories Japan, Inc.) were divided into two groups of 4 mice: mice group fed a standard diet (AIN93G; manufactured by Oriental Yeast Co., Ltd.) (CTL) and mice group fed a KW3110 strain-containing diet (containing 250 mg of the KW3110 strain (the same as prepared in Example 1) in 1 kg of the standard diet on dry weight basis) (KW). The mice had ad libitum access to water and the diet under normal light including visible light.

The period of KW3110 strain ingestion was 3 weeks, and the daily ingestion amount of the KW3110 strain bacteria was about 1 mg. Twenty days after the onset of ingestion, the mice were kept under a dark adaptation condition for one day, and the mice adapted to the dark adaptation condition were evaluated by ERG (electroretinography) with three different light intensities. The difference between the groups were analyzed by t-test, and the asterisk (*) in FIG. 5 represents a level of significance of $P<0.05$.

<Result>

Figure 5:
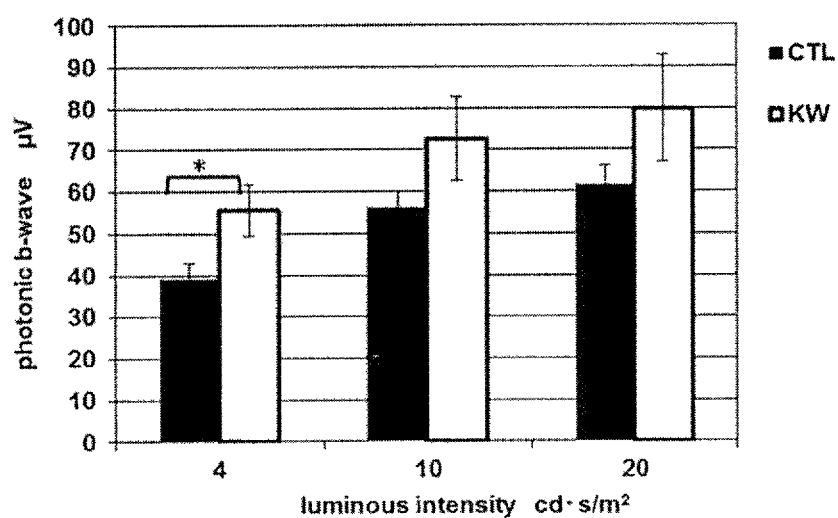
FIG. 5 is a figure showing the amplitudes of electroretinogram b-waves (photonic b-waves) measured in light-adapted mice which are kept under normal visible light. The result of the test using three different visible light intensities (luminous intensities) is shown.

FIG. 5 shows the result of the photonic b-wave measurement. Interestingly, the amplitude of photonic b-wave provided a significantly higher value in the mice group fed a KW3110 strain-containing diet (KW) as compared to mice group fed a standard diet (CTL). This result suggested that ingestion of the KW3110 strain contributes to preventing reduction of visual functions resulting from routine light stimulation.

[Example 7] the Effect of KW3110 to Improve Visual Functions and to Improve Asthenopia in Humans Upon Exposure to Blue Light <Experimental Method>

This study was examined and approved by an outside ethics committee and performed by a third-party institution. This study was a randomized, double-blind, placebo-controlled parallel group study. Specifically, a trial diet (KW3110-containing capsule) or a control diet (KW3110-free capsule) was consumed by male and female healthy subjects with an age of 35 or more to less than 45 years who worked with VDTs for 6 hours or more a day over a period of one year or more and were aware of eye strain and had no chronic disease, and the effect of KW3110 to improve visual functions and to improve eye strain was examined in the subjects.

(1) Test Subjects

Subjects who judged by a physician to be healthy on the basis of a pre-study physical examination were randomly allocated to a trial diet group (Group A) and a control diet group (Group P), such that an equal number of male and female subjects were included in the both groups.

The test subjects were allowed to maintain the same lifestyle as before the enrollment in the study. In other words, the test subjects were basically allowed to continue working with VDTs for 6 hours or more a day.

(2) Intervention

During an ingestion period, the test subjects consumed an assigned test diet (capsule) with cold or warm water once a day on a daily basis. The period of test diet ingestion was 8 weeks.

The test diets are as follows.

(A) Trial diet: KW3110-containing capsule (one capsule contains 50 mg of heat-killed KW3110 bacteria, equivalent to about $5\times10^{10}$ cells). The heat-killed KW3110 bacteria were produced according to a conventional method.

(B) Control diet: KW3110-free capsule (one capsule contains 50 mg of corn starch instead of 50 mg of heat-killed KW3110 bacteria).

(3) Tests (A) Test Items (i) Asthenopia degree (flicker test)

(ii) Questionnaire survey on asthenopia (iii) Questionnaire survey on eye conditions and daily life (B) Test Time Points For the test items (i) and (ii), a VDT load application test was performed on the subjects at their visits before, 4 weeks after, and 8 weeks after the onset of ingestion of the test diets, and the respective test items were performed once before and after the load application test (twice in total; Table 2). Additionally, the test item (iii) was performed once before the VDT load application test at the visits before, 4 weeks after, and 8 weeks after the onset of ingestion of the test diets.

TABLE 2

Summary of the test schedule

| Groups A and P | Ingestion of test diets | | |
|---|---|---|---|
| | Before ingestion | 4 weeks after | 8 weeks after |
| VDT load application | YES | YES | YES |
| Flicker test (before and after the VDT load application) | YES | YES | YES |
| Questionnaire survey on eye conditions and daily life (before the VDT load application) | YES | YES | YES |
| Questionnaire survey on eye strain (before and after the VDT load application) | YES | YES | YES |

A VDT load was applied as described below. The VDT work was playing a game (Where's Wally? in Hollywood)

by using its game application on an iPad mini (registered trademark; Apple Inc.). This work was done by each test subject with an iPad mini on a string around the neck such that the display screen could be kept within 45 cm away from the eyes.

(C) Test Methods
(i) Flicker Test

A Handy Flicker HF-II (registered trademark; Neitz Instruments Co., Ltd.) was used to carry out the measurement three times for each eye by a frequency-increasing method, and the average of the measurements was determined as the observed value.

(ii) Questionnaire Survey on Asthenopia

The questionnaire survey on asthenopia was based on the VAS technique. That is, the test subjects were asked to mark a point by themselves on a 100-mm line with endpoint descriptors of "not at all" at the left end of the line and "worst condition ever experienced or imaginable" at the right end of the line, so that the point best represented, for example, the degree of severity of their eye conditions at the moment when they answered questions on eye conditions. The distance of the marked point from the left end of the 100-mm line was measured, and the obtained value was determined as the observed value (the VAS technique). The questions are as follows.

Questions in the Questionnaire on Asthenopia

"Blurry vition," "Stiffness of the shoulder or lower back," "Ocular fatigue sensation," and "Stuffy head."

(iii) Questionnaire Survey on Eye Conditions and Daily Life (Dry Eye Related Quality of Life Score (DEQS) Y. Sakane et al., JAMA, Ophthalmol. 2013, 131(10), 1331-1338)

The test subjects were asked to answer 16 questions on ocular symptoms and influences on the daily life in the week prior to answering the questionnaire by selecting and recording a score on each question by themselves. From those scores, an ocular symptom score (the questions #1 to 6), an influence score on daily life (the questions #7 to 15), and a total QOL score (the questions #1 to 15) were calculated, and a summary score was also obtained from the answer to the question #16. The questions are as follows.

Questions in the Questionnaire on Eye Conditions and Daily Life

"1) Gritty eye sensation (foreign body sensation)," "2) Dry eye sensation," "3) Ocular pain," "4) Ocular fatigue sensation," "5) Heavy eyelids," "6) Eye redness," "7) Difficulty in keeping eyes open," "8) blurred vision caused by using eyes," "9) Dazzled vision," "10) Deterioration of eye conditions during reading, for example, newspapers, magazines, or books," "11) Deterioration of eye conditions during watching television, or using a personal computer or mobile phone," "12) Poor concentration due to eye conditions," "13) Troubles with business, housework, and study due to eye conditions," "14) A tendency to abandon a desire to go out due to eye conditions," "15) Bad feeling due to eye conditions," and "16) General conditions including eye conditions and troubles in daily life associated therewith."

(4) Evaluation and Analysis

An analysis for all analysis subjects (whole analysis) and an analysis only for subjects with a relatively large degree of eye fatigue (subgroup analysis) were performed.

(A) Numerical Evaluation Methods
(i) Flicker Test and Questionnaire Survey on Asthenopia Measurement values before the VDT load application, measurement values after the VDT load application, and the differences between the measurement values before and after the VDT load application (the values obtained by subtracting the measurement values before the load application from the measurement values after the load application) at the respective test time points were respectively obtained as "the observed values before the VDT load application," "the observed values after the VDT load application," and "the observed values of difference before and after the VDT load application," while "the changes at the time point before the VDT load application," "the changes at the time point after the VDT load application," and "the changes in difference before and after VDT load application" at the respective time points following the onset of ingestion were each determined by subtracting the observed values at the time point prior to the onset of ingestion from the corresponding observed values at the respective time points following the onset of ingestion. The observed values and the changes were evaluated between the both groups by t-test with the Holm correction for multiple comparisons in terms of test time point. Additionally, "the observed values before the VDT load application," "the observed values after the VDT load application," and "the observed values of difference before and after the VDT load application" at the respective time points following the onset of ingestion were evaluated by t-test relative to those values at the time point prior to the onset of ingestion in the respective groups.

(ii) Questionnaire Survey on Eye Conditions and Daily Life

For the scores obtained from the questionnaire survey on eye conditions and daily life (DEQS), the "observed values" before the VDT load application at the respective test time points following the onset of ingestion were obtained, from which the "observed value" before the VDT load application at the time point prior to the onset of ingestion were subtracted to calculate "changes." The "observed values" and the "changes" were compared between the both groups by Mann-Whitney's U test with the Holm correction for multiple comparisons in terms of test time point. Additionally, the observed values at the respective time points following the onset of ingestion were evaluated by one-sample Wilcoxon test.

(B) Subgroup Analysis Methods
(i) Subgroup Analysis in Test Subjects Whose "Ocular Fatigue Sensation" by Questionnaire Survey on Asthenopia was Greater than the Average Score of all Subjects Before VDT Load Application (25 Subjects Who had Observed Values Before the VDT Load Application Equal to or Above the Average of all the Test Subjects, 30.5 mm, at the Time Point Prior to the Onset of Test Diet Ingestion)

The object of this study is to confirm the capability of the trial diet to improve eye fatigue induced by VDT work in subjects who are aware of eye fatigue. Thus, out of the 59 analysis subjects, 25 subjects who had observed values before the VDT load application equal to or above the average of all the subjects in terms of the question on asthenopia "ocular fatigue sensation" at the time point prior to the onset of test diet ingestion were extracted as test subjects who were relatively strongly aware of eye fatigue, among others, and the subgroup analysis was performed on the test subjects.

i) Evaluation of the Effect on Lightening of Fatigue Immediately Induced by VDT Load Application (Fatigue Prevention Effect)

The flicker value is used as an indicator for evaluating eye fatigue or visual functions, and a decrease in flicker value is considered to reflect fatigue or reduced visual functions, and the flicker value is known to be decreased by VDT work (Tsuneto Iwasaki, Ganka (2009) 51 (4), 387-395). For the effect on lightening of fatigue immediately induced by VDT load application (fatigue prevention effect), the observed values of difference before and after the VDT load application and the changes from the observed values at the time point prior to the onset of test diet ingestion were examined in terms of flicker value.

ii) Evaluation of the Conditions in the Shoulder or Lower Back During the Test Period Since stiffness of the shoulder or lower back is known to be a major asthenopia symptom induced by VDT work (Jpn. J. Ind. Health (1986) 28, 87-95), the observed values before the VDT load application and the changes from the observed values at the time point prior to the onset of test diet ingestion were examined in terms of the question on asthenopia "stiffness of the shoulder or lower back" to evaluate the effect to lighten conditions in the shoulder or lower back (the effect to lighten or prevent the influence of VDT work) during the test period.

(ii) Subgroup Analysis in Test Subjects Whose "Ocular Fatigue Sensation" by Questionnaire Survey on Asthenopia was Greater than the Average Score of all Subjects after VDT Load Application (32 Subjects Who had Observed Values after the VDT Load Application Equal to or Above the Average of all the Test Subjects, 55.3 mm, at the Time Point Prior to the Onset of Test Diet Ingestion)

Out of the 59 analysis subjects, 32 subjects who had observed values after the VDT load application equal to or above the average of all the subjects in terms of the question on asthenopia "ocular fatigue sensation" at the time point prior to the onset of test diet ingestion were extracted as test subjects who were relatively strongly aware of eye fatigue after VDT works, and the subgroup analysis was performed on the test subjects.

(iii) Subgroup Analysis in Test Subjects Whose "Stiffness of the Shoulder or Lower Back" by Questionnaire Survey on Asthenopia was Greater than the Average Score of all Subjects Before VDT Load Application (29 Subjects Who had Observed Values Before the VDT Load Application Equal to or Above the Average of all the Test Subjects, 36.1 mm, at the Time Point Prior to the Onset of Test Diet Ingestion)

Out of the 59 analysis subjects, 29 subjects who had observed values before the VDT load application equal to or above the average of all the subjects in terms of the question on asthenopia "stiffness of the shoulder or lower back" at the time point prior to the onset of test diet ingestion were extracted as test subjects who were relatively strongly aware of eye fatigue, among others, and the subgroup analysis was performed on the test subjects.

<Results>

(1) Test Subjects

Thirty one subjects were assigned to both Groups A and P, among which the number of analysis subjects and the average age of the analysis subjects in Group A and Group P were 28 and 40.3±2.7 years (mean±standard deviation), and 31 and 40.6±2.8 years, respectively. The details of the test subjects are shown in Table 3.

TABLE 3

Details of the test subjects

| | Allocation | Analysis subjects |
|---|---|---|
| Group A | Male: 14 subjects | Male: 13 subjects |
| | Female: 17 subjects | Female: 15 subjects |
| Group P | Male: 15 subjects | Male: 15 subjects |
| | Female: 16 subjects | Female: 16 subjects |

(2) Test Results (A) Whole Analysis (i) Flicker Test

The result is shown in Table 4. No significant difference in flicker value was observed between Groups A and P. However, in Group A, the observed values of difference before and after the VDT load application (the values obtained by subtracting the measurement values before the VDT load application from the measurement values after the load application) at the respective time points following the onset of test diet ingestion were larger than that at the time point prior to the onset of test diet ingestion, and the variation was significant at 4 weeks after the onset of test diet ingestion (p=0.013; relative to the variation at the time point prior to the onset of test diet ingestion). This result indicated the possibility that ingestion of the trial diet lightens eye fatigue induced by VDT work.

TABLE 4

Result of the flicker test

| | | flicker value | | | | | |
|---|---|---|---|---|---|---|---|
| | | Before VDT load application | | | After VDT load application | | |
| Group | Values | Before ingestion | 4 weeks after ingestion | 8 weeks after ingestion | Before ingestion | 4 weeks after ingestion | 8 weeks after ingestion |
| A | Observed value (mean ± SD) | 39.13 ± 2.47 | 39.57 ± 2.95 | 39.97 ± 2.94 | 37.68 ± 2.40 | 39.87 ± 2.52 | 39.56 ± 2.92 |
| | Change (mean ± SD) | 0.00 | 0.44 ± 3.42 | 0.85 ± 2.80 | 0.00 | 2.19 ± 2.67 | 1.88 ± 2.96 |
| | One-sample t-test on the observed values relative to those before ingestion | | 0.501 | 0.122 | | 0.000 | 0.002 |
| P | Observed value (mean ± SD) | 39.03 ± 2.62 | 39.45 ± 2.36 | 39.77 ± 2.83 | 38.10 ± 2.97 | 39.24 ± 2.15 | 39.95 ± 2.13 |
| | Change (mean ± SD) | 0.00 | 0.42 | 0.74 | 0.00 | 1.14 ± 2.70 | 1.85 ± 3.42 |
| | One-sample t-test on the observed values relative to those before ingestion | | 0.418 | 0.322 | | 0.026 | 0.005 |
| Two-sample t-test on the observed values (Group A vs Group P) | | 0.883 | 0.863 | 0.789 | 0.557 | 0.303 | 0.561 |
| Two-sample t-test on the changes (Group A vs Group P) | | | 0.979 | 0.911 | | 0.139 | 0.970 |

TABLE 4-continued

Result of the flicker test

| Group | Values | flicker value Difference before and after VDT load application | | |
|---|---|---|---|---|
| | | Before ingestion | 4 weeks after ingestion | 8 weeks after ingestion |
| A | Observed value (mean ± SD) | −1.45 ± 2.38 | 0.30 ± 2.70 | −0.42 ± 2.31 |
| | Change (mean ± SD) | 0.00 | 1.75 ± 3.47 | 1.04 ± 3.15 |
| | One-sample t-test on the observed values relative to those before ingestion | | 0.013 | 0.094 |
| P | Observed value (mean ± SD) | −0.94 ± 2.04 | −0.22 ± 2.03 | 0.17 ± 2.97 |
| | Change (mean ± SD) | 0.00 | 0.72 ± 2.88 | 1.11 ± 4.12 |
| | One-sample t-test on the observed values relative to those before ingestion | | 0.174 | 0.145 |
| Two-sample t-test on the observed values (Group A vs Group P) | | 0.372 | 0.410 | 0.402 |
| Two-sample t-test on the changes (Group A vs Group P) | | | 0.218 | 0.941 |

(ii) Questionnaire Survey on Asthenopia

The result of the questionnaire survey on asthenopia is shown in Table 5. No significant difference was observed between Groups A and P. However, in the both groups, the observed values in terms of "blurred vision" showed a decreasing tendency in the observed values before and after the VDT load application and the observed values of difference before and after the VDT load application, as compared to the observed values at the time point prior to the onset of test diet ingestion, and the tendency was greater in Group A than in the other, and the decreasing tendency in Group A was significant in the subjects before the VDT load application (at 8 weeks after the onset of testing; p=0.044; relative to the observed value at the time point prior to the onset of test diet ingestion).

Additionally, the observed values in terms of "stiffness of the shoulder or lower back" showed a decreasing tendency in the observed values before and after the VDT load application, as compared to the observed values at the time point prior to the onset of test diet ingestion, and the tendency was greater in Group A than in the other, and the decreasing tendency in Group A was significant in the subjects before and after the VDT load application (at 4 and 8 weeks after the onset of testing; relative to the observed values at the time point prior to the onset of test diet ingestion).

Furthermore, the observation values in terms of "ocular fatigue sensation" and "stuffy head" also showed decreasing tendencies in the observed values before and after the VDT load application, as compared to the observed values at the time point prior to the onset of test diet ingestion.

These results suggested the possibility that ingestion of the trial diet alleviates, for example, eye conditions induced by VDT work.

TABLE 5

Result of the questionnaire survey on asthenopia (Blurry vision)

Blurry vision

| | Values | Before VDT load application | | | After VDT load application | | | Difference before and after VDT load application | | |
|---|---|---|---|---|---|---|---|---|---|---|
| | | Before ingestion | 4 weeks after ingestion | 8 weeks after ingestion | Before ingestion | 4 weeks after ingestion | 8 weeks after ingestion | Before ingestion | 4 weeks after ingestion | 8 weeks after ingestion |
| A | Observed value (mean ± SD) | 15.64 ± 21.98 | 9.82 ± 16.92 | 8.14 ± 14.57 | 25.00 ± 26.33 | 19.61 ± 25.40 | 16.71 ± 24.47 | 9.36 ± 16.36 | 9.79 ± 15.44 | 8.57 ± 17.50 |
| | Change (mean ± SD) | 0.00 | -5.82 ± 20.90 | -7.5 ± 18.81 | 0.00 | -5.39 ± 26.67 | -8.29 ± 23.38 | 0.00 | 0.43 ± 20.05 | -0.79 |
| | One-sample t-test on the observed values relative to those before ingestion | | 0.152 | 0.044 | | 0.294 | 0.070 | | 0.911 | 0.831 |
| P | Observed value (mean ± SD) | 13.77 ± 15.84 | 10.16 ± 17.06 | 9.45 ± 15.55 | 26.26 ± 26.10 | 20.58 ± 28.30 | 19.84 ± 25.40 | 12.48 ± 21.10 | 10.42 ± 17.83 | 10.39 ± 14.91 |
| | Change (mean ± SD) | 0.00 | -3.61 ± 9.83 | -4.32 ± 13.15 | 0.00 | -5.68 ± 24.66 | -6.42 ± 21.21 | 0.00 | -2.06 ± 21.57 | -2.10 ± 15.92 |
| | One-sample t-test on the observed values relative to those before ingestion | | 0.050 | 0.077 | | 0.210 | 0.102 | | 0.598 | 0.469 |
| | Two-sample t-test on the observed values (Group A vs Group P) | 0.707 | 0.939 | 0.741 | 0.855 | 0.881 | 0.614 | 0.531 | 0.885 | 0.669 |
| | Two-sample t-test on the changes (Group A vs Group P) | | 0.600 | 0.452 | | 0.966 | 0.748 | | 0.648 | 0.776 |

Result of the questionnaire survey on asthenopia (Stiffness of the shoulder or lower back)

Stiffness of the shoulder or lower back

| | Values | Before VDT load application | | | After VDT load application | | | Difference before and after VDT load application | | |
|---|---|---|---|---|---|---|---|---|---|---|
| | | Before ingestion | 4 weeks after ingestion | 8 weeks after ingestion | Before ingestion | 4 weeks after ingestion | 8 weeks after ingestion | Before ingestion | 4 weeks after ingestion | 8 weeks after ingestion |
| A | Observed value (mean ± SD) | 40.93 ± 24.52 | 29.93 ± 22.86 | 21.07 ± 20.67 | 60.29 ± 21.84 | 44.29 ± 29.50 | 42.11 ± 25.51 | 19.36 ± 16.28 | 14.36 ± 21.18 | 21.04 +/ 19.13 |
| | Change (mean ± SD) | 0.00 | -11.00 ± 24.44 | -19.86 ± 22.52 | 0.00 | -16.00 ± 23.80 | -18.18 ± 20.03 | 0.00 | -5.00 ± 25.30 | 1.68 ± 20.55 |
| | One-sample t-test on the observed values relative to those before ingestion | | 0.025 | 0.000 | | 0.001 | 0.000 | | 0.305 | 0.669 |
| P | Observed value (mean ± SD) | 31.74 ± 23.66 | 23.94 ± 24.92 | 20.23 ± 22.05 | 48.03 ± 31.34 | 42.32 ± 31.40 | 35.48 ± 26.50 | 16.29 ± 25.72 | 18.39 ± 24.78 | 15.26 ± 21.45 |
| | Change (mean ± SD) | 0.00 | -7.81 ± 17.76 | -11.52 ± 14.87 | 0.00 | -5.71 ± 21.09 | -12.55 ± 19.56 | 0.00 | 2.10 ± 18.59 | -1.03 ± 19.54 |
| | One-sample t-test on the observed values relative to those before ingestion | | 0.020 | 0.000 | | 0.142 | 0.001 | | 0.535 | 0.771 |
| | Two-sample t-test on the observed values (Group A vs Group P) | 0.149 | 0.342 | 0.880 | 0.090 | 0.806 | 0.333 | 0.591 | 0.507 | 0.282 |
| | Two-sample t-test on the changes (Group A vs Group P) | | 0.566 | 0.097 | | 0.084 | 0.280 | | 0.222 | 0.606 |

TABLE 5-continued

A vs Group P

Result of the questionnaire survey on asthenopia (Ocular fatigue sensation)

|  | Values | Before VDT load application | | | After VDT load application | | | Difference before and after VDT load application | | |
|---|---|---|---|---|---|---|---|---|---|---|
|  |  | Before ingestion | 4 weeks after ingestion | 8 weeks after ingestion | Before ingestion | 4 weeks after ingestion | 8 weeks after ingestion | Before ingestion | 4 weeks after ingestion | 8 weeks after ingestion |
| A | Observed value (mean ± SD) | 33.79 ± 25.63 | 23.04 ± 25.04 | 16.11 ± 20.64 | 56.71 ± 26.41 | 43.64 ± 290.70 | 37.93 ± 27.75 | 22.93 ± 18.26 | 20.61 ± 21.24 | 21.82 ± 23.38 |
|  | Change (mean ± SD) | 0.00 | −10.75 ± 28.76 | −17.68 ± 24.89 | 0.00 | −13.07 ± 23.90 | −18.79 ± 22.54 | 0.00 | −2.32 ± 27.56 | −1.11 ± 25.54 |
|  | One-sample t-test on the observed values relative to those before ingestion |  | 0.058 | 0.001 |  | 0.007 | 0.000 |  | 0.659 | 0.820 |
| P | Observed value (mean ± SD) | 27.52 ± 23.90 | 16.48 ± 20.48 | 14.97 ± 23.11 | 53.94 ± 26.06 | 42.48 ± 30.37 | 38.16 ± 26.72 | 26.42 ± 22.11 | 26.00 ± 24.19 | 23.19 ± 19.18 |
|  | Change (mean ± SD) | 0.00 | −11.03 ± 16.24 | −12.55 ± 15.22 | 0.00 | −11.45 ± 20.83 | −15.77 ± 16.01 | 0.00 | −0.42 ± 20.45 | −3.23 ± 19.84 |
|  | One-sample t-test on the observed values relative to those before ingestion |  | 0.001 | 0.000 |  | 0.005 | 0.000 |  | 0.910 | 0.372 |
| Two-sample t-test on the observed values (Group A vs Group P) | | 0.335 | 0.274 | 0.843 | 0.686 | 0.883 | 0.974 | 0.514 | 0.369 | 0.805 |
| Two-sample t-test on the changes (Group A vs Group P) | |  | 0.963 | 0.338 |  | 0.782 | 0.553 |  | 0.763 | 0.722 |

Result of the questionnaire survey on asthenopia (Stuffy head)

|  | Values | Before VDT load application | | | After VDT load application | | | Difference before and after VDT load application | | |
|---|---|---|---|---|---|---|---|---|---|---|
|  |  | Before ingestion | 4 weeks after ingestion | 8 weeks after ingestion | Before ingestion | 4 weeks after ingestion | 8 weeks after ingestion | Before ingestion | 4 weeks after ingestion | 8 weeks after ingestion |
| A | Observed value (mean ± SD) | 18.00 ± 22.04 | 10.96 ± 14.29 | 7.75 ± 13.76 | 31.82 ± 27.82 | 23.54 ± 28.70 | 20.25 ± 25.64 | 13.82 ± 22.27 | 12.57 ± 22.83 | 12.50 ± 19.55 |
|  | Change (mean ± SD) | 0.00 | −7.04 ± 25.36 | −10.25 ± 22.34 | 0.00 | −8.29 ± 25.07 | −11.57 ± 23.25 | 0.00 | −1.25 ± 21.70 | −1.32 ± 16.80 |
|  | One-sample t-test on the observed values relative to those before ingestion |  | 0.154 | 0.022 |  | 0.104 | 0.014 |  | 0.763 | 0.680 |

TABLE 5-continued

| | | | | | | | | |
|---|---|---|---|---|---|---|---|---|
| P | Observed value (mean ± SD) | 11.90 ± 20.72 | 7.90 ± 12.87 | 7.81 ± 15.81 | 19.26 ± 26.77 | 18.65 ± 28.67 | 17.45 ± 24.96 | 7.35 ± 15.24 | 10.74 ± 22.59 | 9.65 ± 16.31 |
| | Change (mean ± SD) | 0.00 | −4.00 ± 13.74 | −4.10 ± 14.72 | 0.00 | −0.61 ± 26.60 | −1.81 ± 22.82 | 0.00 | 3.39 ± 28.73 | 2.29 ± 22.67 |
| | One-sample t-test on the observed values relative to those before ingestion | | 0.116 | 0.132 | | 0.900 | 0.663 | | 0.517 | 0.578 |
| | Two-sample t-test on the observed values (Group A vs Group P) | 0.278 | 0.390 | 0.988 | 0.083 | 0.516 | 0.673 | 0.195 | 0.758 | 0.544 |
| | Two-sample t-test on the changes (Group A vs Group P) | | 0.565 | 0.213 | | 0.271 | 0.109 | | 0.491 | 0.494 |

(iii) Questionnaire Survey on Eye Conditions and Daily Life

The result of the questionnaire survey on eye conditions and daily life is shown in Table 6. In the both groups, the observed values showed decreasing tendencies, as compared to the observed values at the time point prior to the onset of test diet ingestion, and the tendencies were greater in Group A than in the other. An influence score on daily life (p=0.027; however, not significant according to the multiple test) was observed in the changes at 8 weeks after the onset of test diet ingestion (obtained by subtracting the observed values at the time point prior to the onset of test diet ingestion from the corresponding observed values at 8 weeks after the onset of ingestion) between the two groups. The result thus indicated the possibility that ingestion of the trial diet relieves the influence of the VDT load on daily life.

TABLE 6

Result of the questionnaire survey on eye conditions and daily life

| | | Ocular symptom score | | | Influence score on daily life | | |
| --- | --- | --- | --- | --- | --- | --- | --- |
| Group | Values | Before ingestion | 4 weeks after ingestion | 8 weeks after ingestion | Before ingestion | 4 weeks after ingestion | 8 weeks after ingestion |
| A | Observed value (mean ± SD) | 30.95 ± 20.24 | 22.92 ± 18.99 | 20.68 ± 18.99 | 19.64 ± 16.41 | 12.50 ± 18.09 | 10.62 ± 16.04 |
| | Change (mean ± SD) | 0.0 | −8.04 ± 13.75 | −10.27 ± 18.86 | 0.0 | −7.14 ± 12.62 | −9.03 ± 12.37 |
| | One-sample t-test on the observed values relative to those before ingestion | | 0.004 | 0.012 | | 0.007 | 0.000 |
| P | Observed value (mean ± SD) | 28.63 ± 21.07 | 19.62 ± 17.12 | 18.55 ± 17.31 | 14.78 ± 14.95 | 12.72 ± 15.26 | 10.30 ± 10.30 |
| | Change (mean ± SD) | 0.0 | −9.00 ± 13.01 | −10.08 ± 10.80 | 0.0 | −2.06 ± 9.99 | −4.48 ± 9.88 |
| | One-sample t-test on the observed values relative to those before ingestion | | 0.001 | 0.000 | | 0.229 | 0.011 |
| | Two-sample Mann-Whitney's U test on the observed values (Group A vs Group P) | 0.653 | 0.442 | 0.690 | 0.228 | 0.470 | 0.295 |
| | Two-sample Mann-Whitney's U test on the changes (Group A vs Group P) | | 0.618 | 0.630 | | 0.071 | 0.027 |

| | | Total QOL score | | | Question #16 (about general conditions) | | |
| --- | --- | --- | --- | --- | --- | --- | --- |
| Group | Values | Before ingestion | 4 weeks after ingestion | 8 weeks after ingestion | Before ingestion | 4 weeks after ingestion | 8 weeks after ingestion |
| A | Observed value (mean ± SD) | 24.17 ± 16.76 | 16.67 ± 17.56 | 14.64 ± 16.68 | 3.46 ± 0.69 | 3.04 ± 0.69 | 3.00 ± 0.67 |
| | Change (mean ± SD) | 0.0 | −7.50 ± 11.89 | −9.52 ± 13.82 | 0.0 | −0.43 ± 0.69 | −0.46 ± 0.74 |
| | One-sample t-test on the observed values relative to those before ingestion | | 0.002 | 0.001 | | 0.007 | 0.003 |
| P | Observed value (mean ± SD) | 20.32 ± 16.01 | 15.48 ± 15.36 | 13.60 ± 12.10 | 3.48 ± 0.57 | 3.16 ± 0.64 | 3.06 ± 0.85 |
| | Change (mean ± SD) | 0.0 | −4.84 ± 9.04 | −6.72 ± 9.05 | 0.0 | −0.32 ± 0.65 | −0.42 ± 0.81 |
| | One-sample t-test on the observed values relative to those before ingestion | | 0.009 | 0.000 | | 0.020 | 0.010 |
| | Two-sample Mann-Whitney's U test on the observed values (Group A vs Group P) | 0.391 | 0.967 | 0.680 | 0.909 | 0.404 | 0.740 |
| | Two-sample Mann-Whitney's U test on the changes (Group A vs Group P) | | 0.563 | 0.452 | | 0.494 | 0.760 |

(B) Subgroup Analyses (i) Subgroup Analysis in Test Subjects Who had Observed Values Before the VDT Work Equal to or Above the Average from all Test Subjects in Terms of the Question on Asthenopia "Ocular Fatigue Sensation" (25 Subjects Who had Observed Values Before the VDT Load Application Equal to or Above the Average of all the Test Subjects, 30.5 mm, at the Time Point Prior to the Onset of Test Diet Ingestion; Group A: 13 Subjects; Group P: 12 Subjects)

The result of the evaluation of the effect on lightening of fatigue immediately induced by VDT load application (fatigue prevention effect) and the result of the evaluation of the conditions in the shoulder or lower back during the test period are shown in Table 7. The observed values of difference before and after the VDT load application in terms of flicker value (the values obtained by subtracting the measurement values before the VDT load application from the measurement values after the load application) in the period of test diet ingestion in Group A was larger than that prior to the onset of ingestion and those in the same period in Group P. In addition, the difference between the both groups was significant in the change at 4 weeks after the onset of ingestion. This result indicated the possibility that eye fatigue immediately induced by VDT load application is lightened (prevented) during the period of trial diet ingestion.

The observation values in terms of subjective symptom of stiffness of the shoulder or lower back before the VDT work in the period of test diet ingestion in Group A were smaller than that prior to the onset of ingestion and those in the same period in Group P. In addition, the difference between the both groups was significant in the change at 8 weeks after the onset of ingestion. This result indicated the possibility that the stiffness of the shoulder or lower back caused by the VDT load application is lightened (prevented) during the period of trial diet ingestion.

TABLE 7

Subgroup analysis in the subjects with relatively strong awareness of eye fatigue (1)

| | | Flicker value Difference before and after VDT load application | | | Question on asthenopia "stiffness of the shoulder or lower back" | | |
|---|---|---|---|---|---|---|---|
| | Values | Before ingestion | 4 weeks after ingestion | 8 weeks after ingestion | Before ingestion | 4 weeks after ingestion | 8 weeks after ingestion |
| A | Observed value (mean ± SD) | −1.49 ± 2.35 | 0.62 ± 2.18 | −0.44 ± 2.47 | 60.77 ± 13.78 | 33.92 ± 21.27 | 26.23 ± 25.02 |
| | Change (mean ± SD) | 0.00 | 2.10 ± 2.94 | 1.05 ± 3.20 | 0.00 | −26.85 19.42 | −34.54 ± 23.31 |
| P | Observed value (mean ± SD) | −0.42 ± 2.48 | −0.92 ± 1.75 | −1.44 ± 3.48 | 50.42 ± 15.80 | 39.00 ± 21.76 | 36.08 ± 25.00 |
| | Change (mean ± SD) | 0.00 | −0.50 ± 2.16 | −1.03 ± 5.27 | 0.00 | −11.42 ± 22.34 | −14.33 ± 15.69 |
| | Two-sample t-test on the observed values (Group A vs Group P) | 0.279 | 0.066 | 0.409 | 0.093 | 0.561 | 0.335 |
| | Two-sample t-test on the changes (Group A vs Group P) | | 0.020 | 0.241 | | 0.078 | 0.019 |

(ii) Subgroup Analysis in Test Subjects Who had Observed Values after the VDT Work Equal to or Above the Average from all Test Subjects in Terms of the Question on Asthenopia "Ocular Fatigue Sensation" (32 Subjects Who had Observed Values after the VDT Load Application Equal to or Above the Average of all the Test Subjects, 55.3 mm, at the Time Point Prior to the Onset of Test Diet Ingestion; Group A: 15 Subjects; Group P: 17 Subjects)

The result of the evaluation of the effect on lightening of fatigue immediately induced by VDT load application (fatigue prevention effect) and the result of the evaluation of the conditions in the shoulder or lower back during the test period are shown in Table 8. The observed values of difference before and after the VDT load application in terms of flicker value (the values obtained by subtracting the measurement values before the VDT load application from the measurement values after the load application) in the period of test diet ingestion in Group A was larger than that prior to the onset of ingestion and those in the same period in Group P. In addition, the difference between the both groups was significant in the change at 4 weeks after the onset of ingestion. This result indicated the possibility that eye fatigue immediately induced by VDT load application is lightened (prevented) during the period of trial diet ingestion.

The observation values in terms of subjective symptom of stiffness of the shoulder or lower back before the VDT work in the period of test diet ingestion in Group A were smaller than that prior to the onset of ingestion. Moreover, the changes were larger in Group A as compared to Group P. This result indicated the possibility that the stiffness of the shoulder or lower back caused by the VDT load application is lightened (prevented) during the period of trial diet ingestion particular in subjects who are relatively strongly aware of eye fatigue after the load application.

TABLE 8

Subgroup analysis in the subjects with relatively strong awareness of eye fatigue (2)

| Group | Values | Flicker value Difference before and after VDT load application | | | Question on asthenopia "stiffness of the shoulder or lower back" | | |
|---|---|---|---|---|---|---|---|
| | | Before ingestion | 4 weeks after ingestion | 8 weeks after ingestion | Before ingestion | 4 weeks after ingestion | 8 weeks after ingestion |
| A | Observed value (mean ± SD) | −1.71 ± 2.70 | 0.47 ± 1.81 | −0.64 ± 2.56 | 56.93 ± 17.96 | 42.73 ± 21.28 | 29.80 ± 21.40 |
| | Change (mean ± SD) | 0.00 | 2.18 ± 2.92 | 1.07 ± 3.19 | 0.0 | −14.20 ± 30.04 | −27.13 ± 23.96 |
| P | Observed value (mean ± SD) | −0.47 ± 2.29 | −0.76 ± 1.94 | −0.75 ± 3.39 | 43.71 ± 23.61 | 34.12 ± 27.15 | 30.72 ± 24.31 |
| | Change (mean ± SD) | 0.00 | −0.29 ± 2.79 | −0.27 ± 4.83 | 0.0 | −9.59 ± 20.77 | −13.00 ± 15.52 |
| | Two-sample t-test on the observed values (Group A vs Group P) | 0.170 | 0.074 | 0.926 | 0.088 | 0.330 | 0.912 |
| | Two-sample t-test on the changes (Group A vs Group P) | | 0.021 | 0.355 | | 0.614 | 0.054 |

(iii) Test Subjects Who had Observed Values Before the VDT Work Equal to or Above the Average from all Test Subjects in Terms of the Question on Asthenopia "Stiffness of the Shoulder or Lower Back" (29 Subjects Who had Observed Values Before the VDT Load Application Equal to or Above the Average of all the Test Subjects, 36.1 mm, at the Time Point Prior to the Onset of Test Diet Ingestion)

The result of the evaluation of flicker value during the test period is shown in Table 9. The observed values of difference before and after the VDT load application in terms of flicker value (the values obtained by subtracting the measurement values before the VDT load application from the measurement values after the load application) in the period of test diet ingestion in Group A was larger than that prior to the onset of ingestion and those in the same period in Group P. In addition, the difference between the both groups was significant in the change at 4 weeks after the onset of ingestion. This result indicated the possibility that eye fatigue immediately induced by VDT load application is lightened (prevented) during the period of trial diet ingestion.

TABLE 9

Subgroup analysis in the subjects with relatively strong awareness of eye fatigue (3)

| | | Flicker value Difference before and after VDT load application | | |
|---|---|---|---|---|
| Group | Values | Before ingestion | 4 weeks after ingestion | 8 weeks after ingestion |
| A | Observed value (mean ± SD) | −1.78 ± 2.65 | 0.38 ± 2.03 | −0.38 ± 2.31 |
|   | Change (mean ± SD) | 0.00 | 2.16 ± 3.23 | 1.40 ± 3.17 |
| P | Observed value (mean ± SD) | −0.45 ± 2.33 | −0.90 ± 1.92 | −0.88 ± 3.50 |
|   | Change (mean ± SD) | 0.00 | −0.45 ± 2.56 | −0.43 ± 5.10 |
|   | Two-sample t-test on the changes (Group A vs Group P) |  | 0.024 | 0.253 |

<Conclusion>

The ingestion of the trial diet prevented the reduction of flicker value from before to after the load application and improved subjective symptoms of stiffness of the shoulder or lower back perceived before the load application in the test subjects who were relatively strongly aware of eye fatigue (particularly, test subjects who were relatively strongly aware of eye fatigue associated with VDT work). Thus, the ingestion of the trial diet was indicated to have a positive effect on asthenopia.

The invention claimed is:

1. A method for suppressing or improving eye fatigue or asthenopia, comprising feeding or administering an effective amount of a lactic acid bacterium to a mammal, including a human, wherein said lactic acid bacterium is *Lactobacillus paracasei* strain KW3110.

2. The method according to claim 1, wherein said eye fatigue is induced by light stimulation.

3. The method according to claim 2, wherein said light causing said light stimulation has a wavelength of 380 nm to 530 nm.

4. The method according to claim 1, wherein the *Lactobacillus paracasei* strain KW3110 is provided in the form of a food.

5. The method according to claim 1, wherein the *Lactobacillus paracasei* strain KW3110 is provided in the form of a supplement.

* * * * *